US008766634B2

(12) United States Patent
Blank et al.

(10) Patent No.: US 8,766,634 B2
(45) Date of Patent: Jul. 1, 2014

(54) METHOD AND DEVICE OF ESTIMATING A DOSE OF IONIZING RADIATION

(75) Inventors: Aharon Blank, Kfar-Vradim (IL); Ygal Twig, Petach-Tikva (IL)

(73) Assignee: Technion Research & Development Foundation Limited, Haifa (IL)

( * ) Notice: Subject to any disclaimer, the term of this patent is extended or adjusted under 35 U.S.C. 154(b) by 450 days.

(21) Appl. No.: 13/263,852

(22) PCT Filed: Apr. 15, 2010

(86) PCT No.: PCT/IL2010/000303
§ 371 (c)(1),
(2), (4) Date: Oct. 11, 2011

(87) PCT Pub. No.: WO2010/122546
PCT Pub. Date: Oct. 28, 2010

(65) Prior Publication Data
US 2012/0025828 A1 Feb. 2, 2012

Related U.S. Application Data

(60) Provisional application No. 61/170,940, filed on Apr. 20, 2009.

(51) Int. Cl.
*G01V 3/00* (2006.01)
(52) U.S. Cl.
USPC .......................................... 324/309; 324/315
(58) Field of Classification Search
None
See application file for complete search history.

(56) References Cited

U.S. PATENT DOCUMENTS

| 6,696,040 | B2 * | 2/2004 | Driehuys ........................ 424/9.3 |
| 6,791,326 | B2 * | 9/2004 | Gerald et al. ................. 324/318 |
| 7,357,917 | B2 * | 4/2008 | Driehuys ........................ 424/9.3 |
| 2003/0117141 | A1 * | 6/2003 | Gerald et al. ................. 324/322 |
| 2004/0251899 | A1 | 12/2004 | Swartz et al. |
| 2005/0021019 | A1 | 1/2005 | Hashimshony et al. |

FOREIGN PATENT DOCUMENTS

WO WO 2010/122546 10/2010

OTHER PUBLICATIONS

International Preliminary Report on Patentability Dated Nov. 3, 2011 From the International Bureau of WIPO Re. Application No. PCT/IL2010/000303.
International Search Report and the Written Opinion Dated Aug. 20, 2010 From the International Searching Authority Re. Application No. PCT/IL2010/000303.

(Continued)

*Primary Examiner* — Brij Shrivastav

(57) ABSTRACT

A device of estimating a dose of ionizing radiation absorbed in an intra bone volume. The device comprises a static magnetic field source adapted to generate a substantially static magnetic field in a probing space having a volume of less than 2 cubic millimeter ($mm^3$), the probing space being placed in front of a distal end of static magnetic field source, a micro resonator mounted in adjacent to the distal end, and at least one transmission line which feeds the resonator so as to generate an microwave magnetic field at the probing space and to transmit a signal returned from said microwave magnetic field and indicative of radiation induced paramagnetic defects in said probing space so as to allow a spectrometer to compute a dose of ionizing radiation absorbed in a portion of a bone placed in the probing space according to an analysis of the signal. The static magnetic field source being sized and shaped to maneuver the probing space to overlap with an intra bone volume of the bone.

24 Claims, 6 Drawing Sheets

(56) References Cited

OTHER PUBLICATIONS

Blümich et al. "Mobile Single-Sided NMR", Progress in Nuclear Magnetic Resonance Spectroscopy, XP022589395, 52(4): 197-269, May 1, 2008. P.254, 1-h Col., § 2, Fig.7.

Swartz et al. "In Vivo EPR for Dosimetry", Radiation Measurements, XP022264801, 42(6-7): 1075-1084, Jul. 1, 2007.

* cited by examiner

METHOD AND DEVICE OF ESTIMATING A DOSE OF IONIZING RADIATION

RELATED APPLICATIONS

This application is a National Phase of PCT Patent Application No. PCT/IL2010/000303 having International filing date of Apr. 15, 2010, which claims the benefit of priority of U.S. Provisional Patent Application No. 61/170,940, filed on Apr. 20, 2009. The content of the above applications are all incorporated herein by reference.

FIELD AND BACKGROUND OF THE INVENTION

The present invention, in some embodiments thereof, relates to method and device of microwave spectroscopic analysis and, more particularly, but not exclusively, to method and device of ionizing radiation dosimetry.

Electron paramagnetic resonance (EPR), also denoted as electron spin resonance (ESR), is a technique used for studying chemical species that have one or more unpaired electrons, such as organic and inorganic free radicals or inorganic complexes possessing a transition metal ion.

This technique has been applied to radiation dose reconstruction, identification of irradiated food, radiation therapy, radiation processing quality assurance and archaeological dating. Tooth enamel, dentine, bone and alanine are some examples of materials successfully applied to these applications; see Desrosiers, M. F., Schauer, D. A., 2001. Electron paramagnetic resonance (EPR) biodosimetry. Nucl. Instrum. Methods B 184/1-2, 219-228, which is incorporated herein by reference.

The EPR signal of unpaired electron is acquired by an EPR spectrometer analyses a signal intercepted from a microwave magnetic field to detect the presence of unpaired electrons. Ionizing radiation generates large numbers of unpaired electron species. While most of these react immediately and disappear, in some materials in which diffusion is limited, the unpaired electrons can persist for long periods and are often related to as "paramagnetic defects". The concentration of these radiation-induced paramagnetic defects is proportional to the absorbed dose and the EPR spectrometer measures these defects. This is performed by the resonance absorption of electromagnetic energy at electron-spin transitions when the sample is placed under external static magnetic field. In order to resolve different electron-spin levels a static magnetic field is applied. In the simplest and most typical situation unpaired electrons of free radicals have spin (or magnetic moment) equal to ½. In a magnetic field there are two magnetic levels, +½ and −½ with two different energies. The level with spin equal to −½ has less energy than the level with spin +½. The transition between these levels is possible under a resonance condition (when the applied microwave magnetic field frequency is equal to the energy difference E=hv), for example as described in David A. Schauer, Electron paramagnetic resonance (EPR) in medical dosimetry, Radiation Measurements 41 (2007) S117-S123, which is incorporated herein by reference.

Until recently the use of this technology for dosimeter was limited to isolated samples. However, recent EPR developments have made in vivo measurements possible.

Such measurements allow determining the magnitude of the exposure of individuals to ionizing radiation in a dose that could cause direct clinical effects. Currently there are several known devices and methods for in vivo EPR measurements of radiation-induced paramagnetic defects which differentiate among doses sufficiently for classifying individuals into categories for treatment, with sufficient accuracy to facilitate decisions on medical treatment.

For example, U.S. Pat. No. 7,084,628 filed on Aug. 12, 2010, describes in vivo methods and apparatus for radiation dosimetry assessment in individuals exposed to potentially harmful radiation, based on measurements in-situ of the teeth. The in vivo dosimetry assessment methods and apparatus utilize EPR techniques and employ an apparatus comprising an integrated EPR spectrometer system, an ergonomic magnet and a constructed resonator structure. This document describes a stationary dosimetry assessment apparatus which is portable as it withstands potentially adverse mechanical effects of transportation and deployment in the field. This apparatus is configured with a power supply that is compatible with both conventional AC line voltages and/or other sources of power suitable for field conditions and may be easily operated by minimally trained technicians to quickly generate a readout of estimated radiation exposure dose.

SUMMARY OF THE INVENTION

According to some embodiments of the present invention there is provided a device of estimating a dose of ionizing radiation absorbed in an intra bone volume. The device comprises a static magnetic field source adapted to generate a substantially static magnetic field in a probing space having a volume of less than 2 cubic millimeter ($mm^3$), the probing space being placed in front of a distal end of static magnetic field source, the static magnetic field source being sized and shaped to maneuver the probing space to overlap with an intra bone volume of the bone, a micro resonator mounted in adjacent to the distal end, and one or more transmission lines which feeds the resonator so as to generate an microwave magnetic field at the probing space. The micro resonator acquires, from the probing space, a signal returned from to the generated microwave magnetic field and indicative of radiation induced paramagnetic defects in the probing space so as to allow a spectrometer to compute a dose of ionizing radiation absorbed in a portion of a bone placed in the probing space according to an analysis of the signal Optionally, the signal is an electron spin resonance (ESR) signal.

Optionally, the static magnetic field source is adapted to form the static magnetic field at a distance of at least 3 mm in front of the distal end.

Optionally, the static magnetic field source having a diameter of less than 5 centimeter (cm).

Optionally, the static magnetic field source having a longitudinal dimension of less than 15 centimeter (cm).

Optionally, the device further comprises a handle for allowing a user to manually locate the distal end in proximity to the bone.

Optionally, the static magnetic field having at least 0.2 Tesla (T) in a homogeneity level between 50 and 500 parts per million (ppm) in a region of less than 1 $mm^3$.

Optionally, the static magnetic field having a gradient in a range between about 0.1 T/m and about 10 T/m along a main axis of the probing space.

Optionally, the probing space having a diameter of less than about 1 mm and a height of less than about 0.5.

Optionally, the resonator is annular.

More optionally the static magnetic field is substantially maximal at a point just above the center of the resonator.

Optionally, the resonator is a dielectric resonator.

Optionally, the spectrometer comprises an electron paramagnetic resonance (EPR) spectrometer.

Optionally, the static magnetic field source comprises one or more elongated magnetic elements in a tubular formation having a central longitudinal axis, the resonator being mounted on the longitudinal axis.

Optionally, the resonator operates at a frequency between 2 GHz and 18 GHz.

According to some embodiments of the present invention there is provided a method of estimating a dose of ionizing radiation absorbed in an intra bone volume. The method comprises generating a magnetic field of having at least one of a gradient in a range between about 0.1 Tesla (T)/meter (m) and about 10 T/m along a main axis of the probing space and at least 0.2 T with homogeneity in a range of between 50 and 500 parts per million (ppm), the magnetic field being in a region of less than 2 cubic millimeter ($mm^3$) in intra bone volume of a bone, generating an microwave magnetic field at the region, and acquiring a signal indicative of radiation induced paramagnetic defects in the probing space from the region, and analyzing the signal, to compute a dose of ionizing radiation absorbed in an intra bone volume of the bone.

Optionally, the bone is a single tooth.

More optionally, the single tooth is a foretooth.

Optionally, the generating comprises resonating an electromagnetic (EM) energy at a frequency between 2 GHz and 18 GHz.

Optionally, the method further comprises displaying the radiation dose.

Optionally, the analyzing comprises analyzing an electron paramagnetic resonance (EPR) signal from the region.

Optionally, the dose is a minimal measurable radiation dose of less than 0.25 Gray (Gy) in the region.

According to some embodiments of the present invention there is provided a handheld probe of estimating a dose of ionizing radiation absorbed in an intra bone volume. The handheld probe comprises a static magnetic field source having elongated magnetic element(s) in a tubular formation having a first diameter of less than 5 centimeters, the static magnetic field source being adapted to generate a substantially static magnetic field in a probing space in front of a distal end of the elongated magnetic element(s), a micro resonator mounted in adjacent to the distal end and having a second diameter smaller than the first diameter, and one or more transmission lines which feed the resonator so as to generate an microwave magnetic field at the probing space. The micro resonator acquires a signal returned from the microwave magnetic field at the probing space and indicative of radiation induced paramagnetic defects in the probing space to allow a spectrometer to compute a dose of ionizing radiation absorbed in a tooth placed in the probing space according to an analysis of the signal.

Optionally, each elongated magnetic element is less than 15 centimeters (cm) long.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a device of estimating a dose of ionizing radiation absorbed in a portion of a bone such as a tooth, according to some embodiments of the present invention;

FIG. 2 is a schematic illustration of the device of FIG. 1 when it is manually maneuvered to place the magnetic field to overlap an intra bone volume, according to some embodiments of the present invention;

FIG. 3 is an exemplary static magnetic field source that is adapted to form a magnetic field, according to some embodiments of the present invention;

FIG. 4 is an illustration of the exemplary magnetic field generated by the exemplary static magnetic field source of FIG. 3, according to some embodiments of the present invention;

FIG. 5 is a graph depicting the homogeneity of the magnetic field of FIG. 4, according to some embodiments of the present invention;

Figure 6:
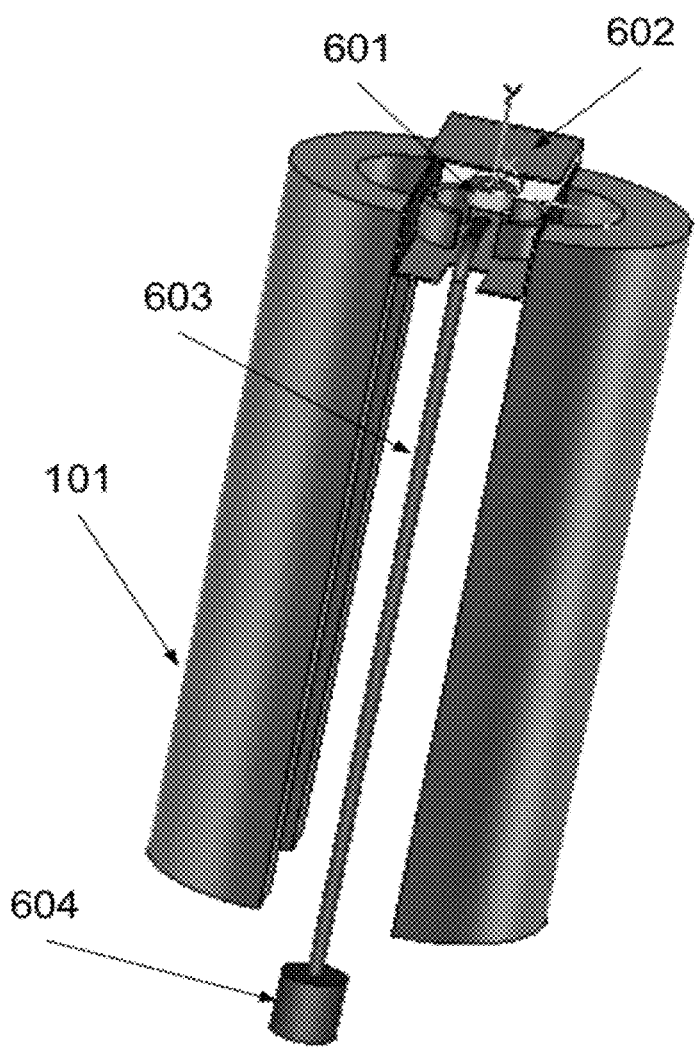
Figure 7:
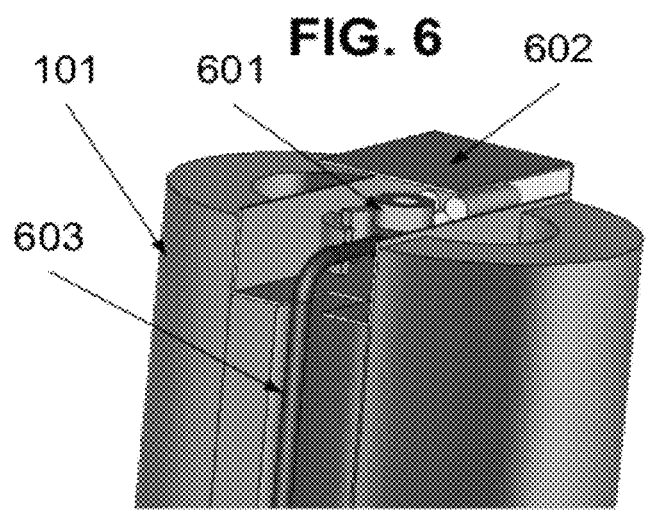
Figure 8:
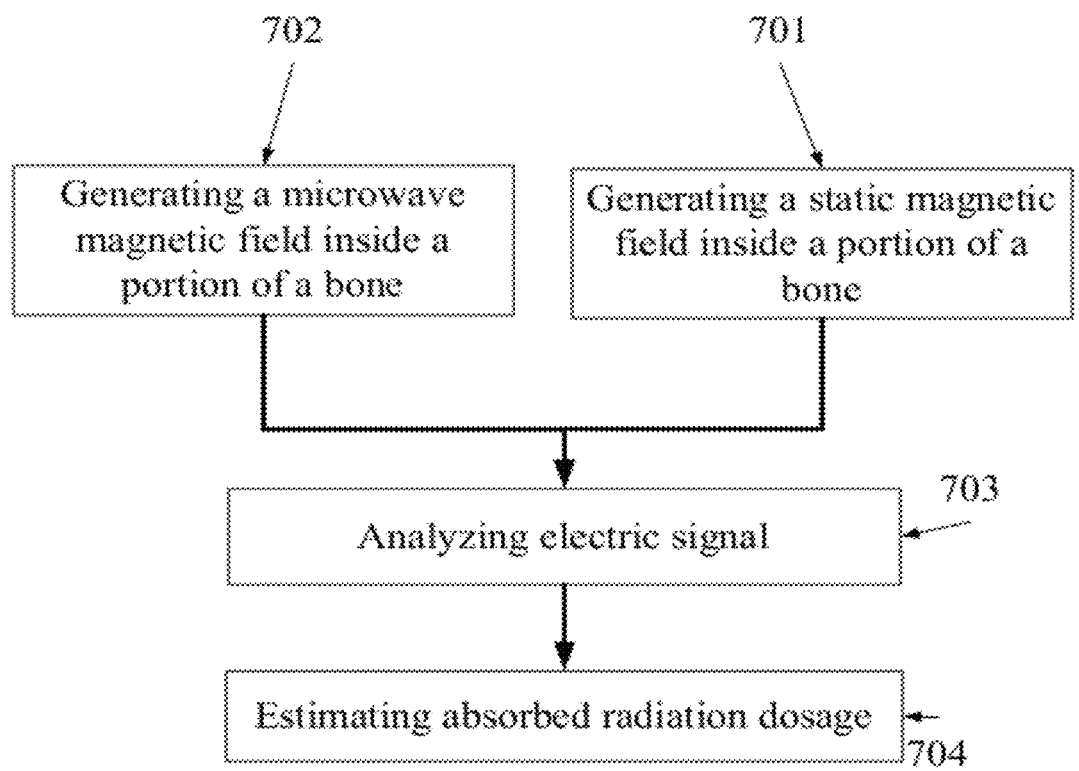

FIGS. 6 and 7 which are respectively a schematic illustration of an exemplary device of estimating a dose of ionizing radiation absorbed in a single tooth and a blowup of its distal end, according to some embodiments of the present invention; and FIG. 8 is a flowchart of a method of estimating a dose of ionizing radiation absorbed in a portion of a bone, according to some embodiments of the present invention.

DESCRIPTION OF EMBODIMENTS OF THE INVENTION

The present invention, in some embodiments thereof, relates to method and device of microwave spectroscopic analysis and, more particularly, but not exclusively, to method and device of ionizing radiation dosimetry.

According to some embodiments of the present invention there is provided methods and devices of estimating a dose of ionizing radiation absorbed in a tooth. The methods and devices are based on an analysis, such as an analysis of EPR signal, of readings from a limited intra bone volume having a volume of less than 2 cubic millimeter (mm$^3$), for example less than 1 mm$^3$. The intra bone volume is optionally of a single foretooth, such as lower or upper incisor or canine tooth. In use, a static magnetic field and a microwave magnetic field are generated at the intra bone volume. The fields are optionally generated using a handheld magnetic generator, having a resonator at its distal end. The handheld magnetic generator is sized and shaped for being manually maneuvered in a manner that allows an operator to the distal end in proximity to and/or in touch with a selected foretooth.

According to some embodiments of the present invention there is provided a device that includes a static magnetic field source with a desired spatial dependence that generates a substantially static magnetic field in front of its distal end. The magnetic field is optionally at a probing space having the desired spatial field dependence at a volume of less than 2 cubic millimeters (mm$^3$). The device also includes a microwave micro resonator, optionally dielectric, which is mounted in adjacent to the distal end and a transmission line which feeds the micro resonator so as to generate a microwave magnetic field at the probing space. The microwave field excites the spins and their emitted signal is acquired by the same resonator. The desired static field profile can be with specific homogeneity and/or with specific gradient along the probe axis. The magnitude of the signal allows one to compute a dose of ionizing radiation absorbed in a bone portion placed in the probing space, for example a tooth.

According to some embodiments of the present invention there is provided a method of estimating a dose of ionizing radiation absorbed in an intra bone volume. The method includes generating a static magnetic field with desired spatial dependence with mean value of about 0.2 Tesla (T) or more in a region of less than 2 mm$^3$ in an intra bone volume of a bone portion, such as a single tooth. The magnetic field can be homogenous with homogeneity of 50-500 parts per million (ppm), or can have a gradient in the range of 0.1-10 T/m along the probe main axis. Now, a microwave magnetic field is generated in the region, for example as outlined above and described below. The microwave magnetic field is optionally generated by a microwave source (which is part of the EPR spectrometer) having a frequency between about 2 GHz and 18 GHz.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
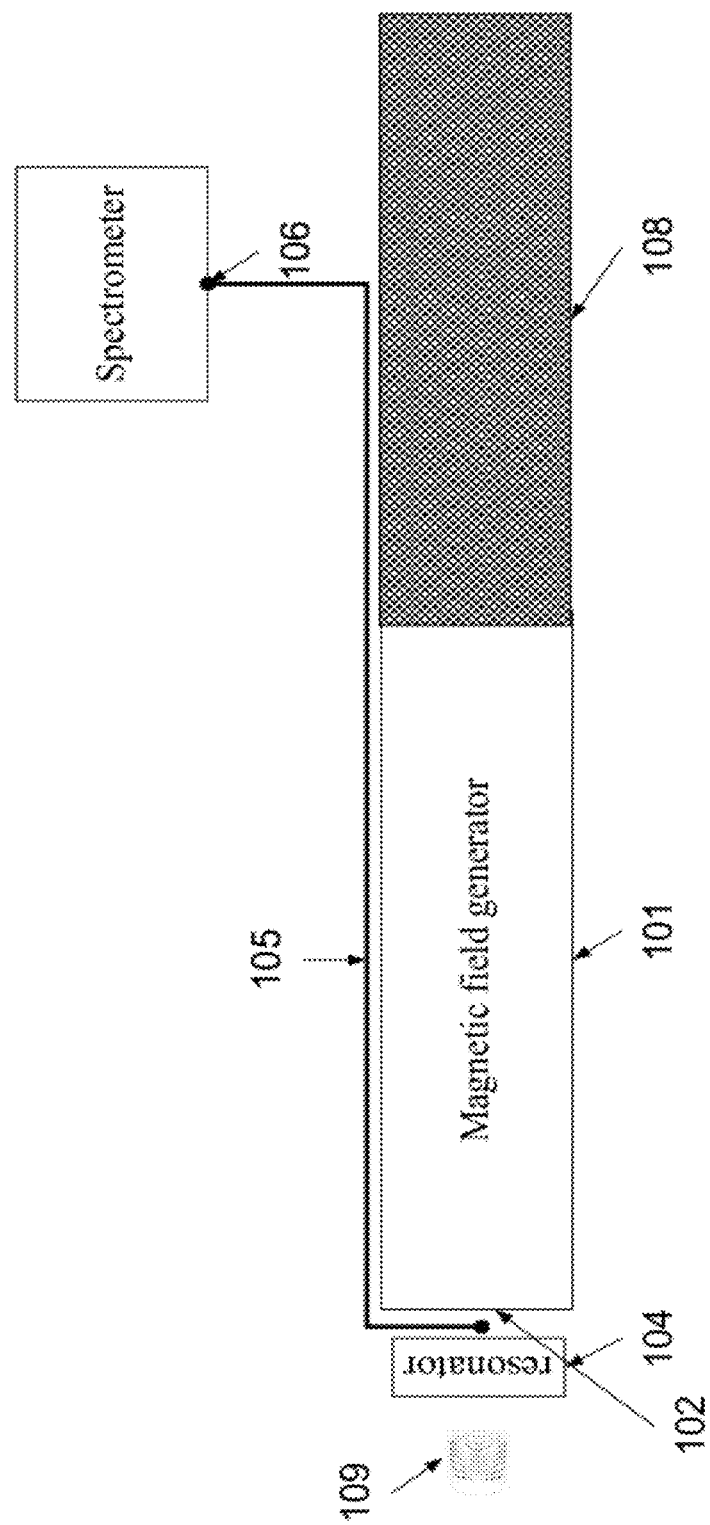

Reference is now made to FIG. 1, which is a schematic illustration of a device 100, optionally handheld device 100, of estimating a dose of ionizing radiation absorbed in a portion of a bare bone, such as single tooth and/or a bone that is attached to the skin of an examinee, according to some embodiments of the present invention. As further described below, the device 100 is designed to measure, in vivo, the dose of ionizing radiation absorbed in an intra bone volume of less than 2 cubic millimeter (mm$^3$), for example about 1 mm$^3$, of a bone portion, such as a single tooth, for example the foretooth. Optionally, in use, the intra bone volume is completely at the tooth enamel portion. In such an embodiment, as the volume of the probing space and the content thereof, during a dosimetry analysis process, for example EPR analysis process, is set in advance. In such n embodiment, the EPR signal, which is proportional to the total number of paramagnetic centers, directly leads to the concentration of the paramagnetic centers, which is linearly proportional to the measured radiation dose. This is different from current in vivo measurement methods that estimate the dose of ionizing radiation from the EPR signal of the entire tooth volume, or from a number of teeth, where the total enamel volume is not known, so it is hard to normalize the overall signal and find the spin concentration (the spectral shape does not change with concentration for most relevant doses of radiation). Furthermore, when the radiation is read from the entire tooth, considerable signal may originate from the surface of the enamel and not from the bulk due to mechanical defects and UV-induced radiation and/or tooth cavities, which further complicate the calculation of the radiation dose according to the concentration of paramagnetic centers.

Figure 2:
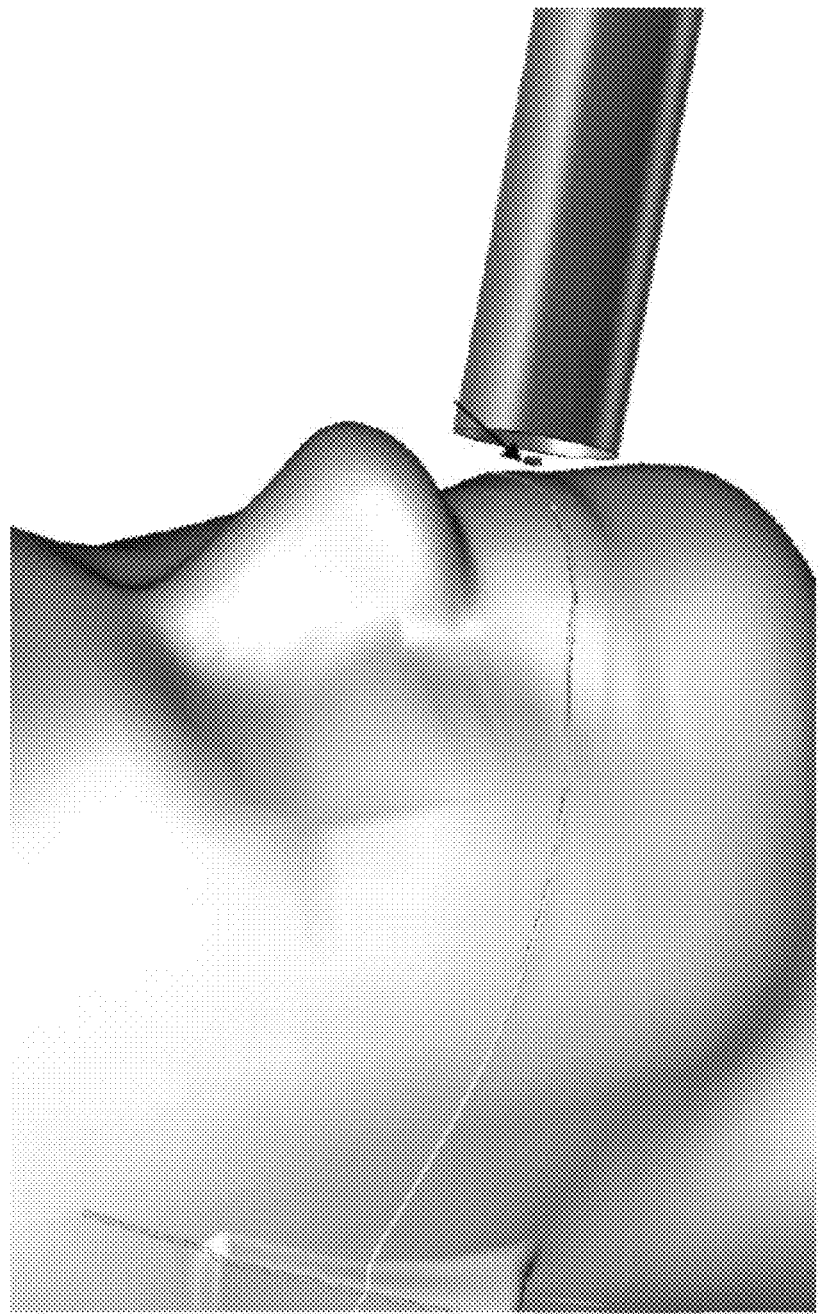

The device 100 includes a static magnetic field source 101, which optionally includes a magnet, permanent or electromagnet, having a one-sided flux, which may be referred to herein as a one sided magnet. The magnetic field source 101 is adapted to generate a substantially static magnetic field having a volume with desirable spatial filed dependence of less than 2 mm$^3$ in front of the static magnetic field source 101 and/or at its distal end 102. Optionally, the static magnetic field source 101 is adapted to generate a magnetic field in front of the distal end 102, for example at a distance of between about 1 mm and about 10 mm from the distal end 102, for example about 5 mm, as shown at 109. The static magnetic field source 101 is sized and shaped to that it may be manually maneuvered in proximity and/or in the mouth, so that the magnetic field is manually placed to overlap an intra bone volume of a certain tooth, such as a foretooth, for example lower or upper incisor or canine tooth. As such, the diameter of the static magnetic field source 101 is optionally less than about 15 centimeters (cm), for example about 10 cm, about 5 cm, about 3 cm or any intermediate or shorter diameter and having a length of between about 5 cm and 15 cm. For example, FIG. 2 depicts a device, such as 100, which is manually maneuvered to place the magnetic field to overlap an intra bone volume of the incisor.

The static magnetic field source 101 is sized and shaped to form the desired static magnetic field centered about a region, which may be referred to as a probing space, in front of a distal end of the static magnetic field source 101. The region has a volume of less than 2 mm$^3$, for example, a cylindrical volume having a 1 mm diameter and 0.5 mm height, and therefore may overlap completely with intra bone volume of a single tooth.

Figure 3:
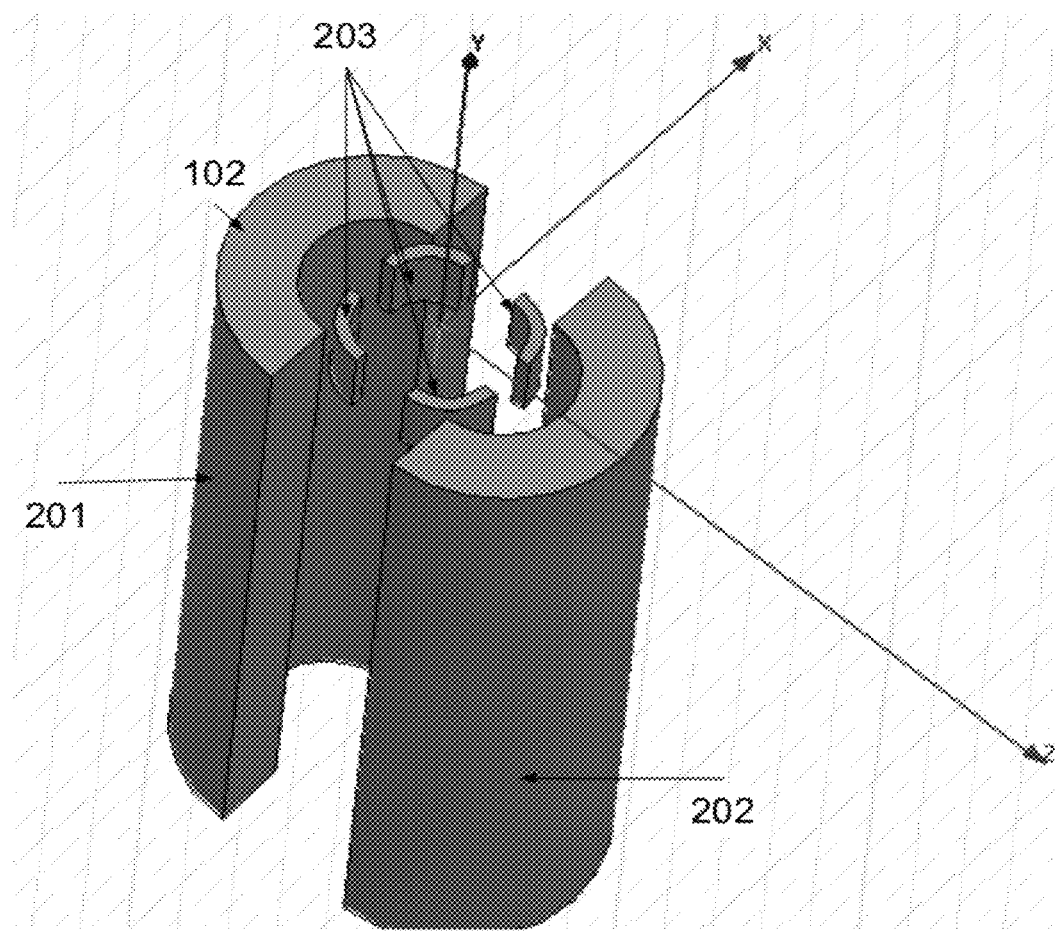
Figure 4:
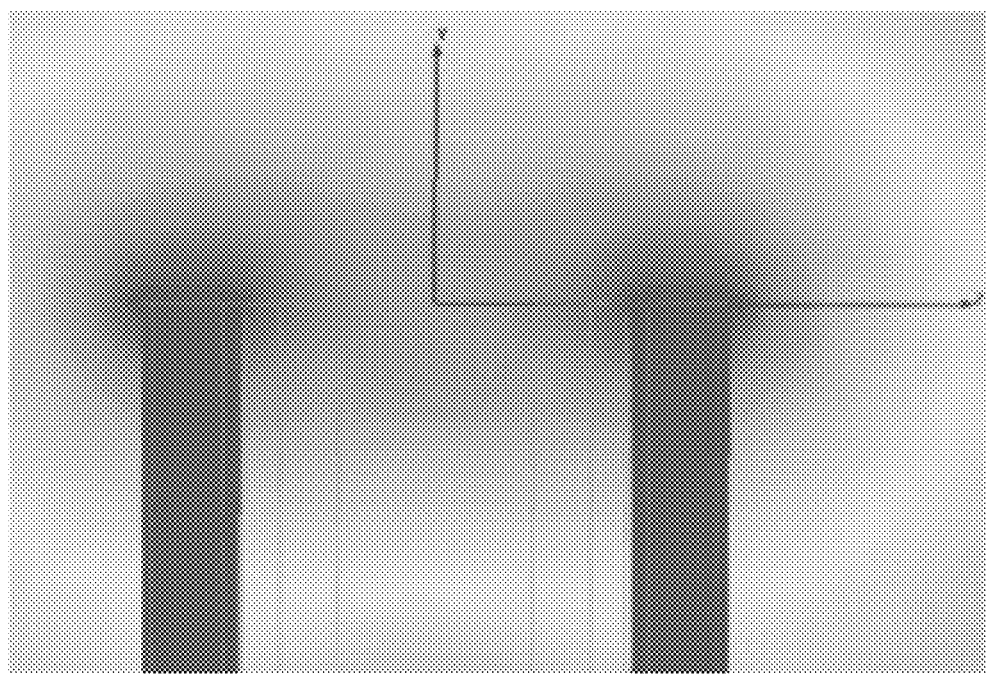
Figure 5:
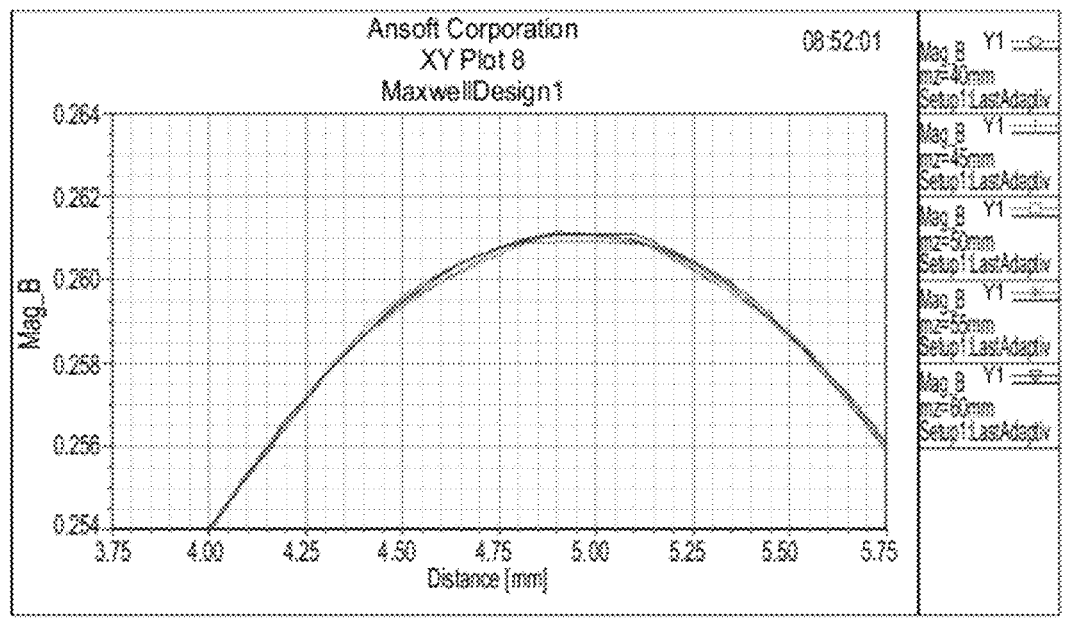

Reference is now also made to FIG. 3, which is an exemplary static magnetic field source 101 that is adapted to form a magnetic field of about 0.261 Tesla (T) having homogeneity of about 100 parts per million (ppm) in a region of less than 1 mm$^3$ at a distance of between 4.75 mm and 5.25 mm from the distal end 102 of the exemplary static magnetic field source 101, according to some embodiments of the present invention. FIG. 4 is an illustration of the exemplary magnetic field generated by the exemplary static magnetic field source 101 depicted in FIG. 3. FIG. 5 is a graph depicting the homogeneity of the magnetic field of about 0.261 T (plotted as a function of the distance from the distal end).

It should be noted that other magnetic fields of more than 0.2 T having homogeneity in a range of about 50 and 500 ppm in a region having a volume of less than 2 mm3 at a distance of between 1 mm and 10 mm from the distal end 102 of the exemplary static magnetic field source 101 may be generated when a different static magnetic field sources are used. Alternatively, one may prefer to have a desired gradient of between about 0.1 T/m and about 10 T/m in the probing space. This can be achieved in the current example by shifting the region of interest either before or after the homogenous region.

As depicted in FIG. 3, the exemplary static magnetic field source 101 includes two elongated magnetic elements 201, 202 which are arranged in a tubular formation. The elongated magnetic elements 201-202, which are optionally curved elements having a semicircular profile, are mounted along a central longitudinal axis, marked as axis y, concavely to one another. It should be noted that any number of elongated magnetic elements may be used. The static magnetic field source 101 has a plurality of shim magnets 203 which are mounted around the central longitudinal axis, in proximity to the distal end 102, concavely to one another. As an option the static magnetic field sources are made from permanent magnets made of high remanence rare earth materials such as NdFeBr or SmCo, or temperature compensated SmCo (for low dependence of field upon temperature). The magnetization direction of the elongated magnetic element 201 is in the +y direction while that of the elongated magnetic element 202 is in the −y direction. Thereby the magnetic field direction in the region of interest is primarily along the z-axis in the image. Furthermore, the shim magnets 203 may have magnetization directed along the +y or −y or any angle in between, so as to shape the required magnetic field spatial dependence static magnetic field source The plurality of shaping elements 203 are encircled by the elongated magnetic elements 201, 202. It should be noted that other shaping elements, which are optionally selected according to known methods of shaping magnetic fields, may be used. For example the used method is a method for shaping one sided field to achieve a required spatial dependence as defined in "Single-sided mobile NMR with a Halbach magnet" by Wei-Hao Chang et.al. which is, together with references thereof, incorporated by reference.

Reference is now made, once again, to FIG. 1. The device 100 further includes a micro resonator 104 mounted in adjacent to the distal end 102 and optionally sized and shaped for engagement with a single tooth. For example, the micro resonator 104 is an annular resonator, optionally comprised from a single ring having an outside diameter of about 2.5 mm and an inside diameter of about 1 mm and a height of about 0.5 mm. The micro resonator 104 is optionally mounted in front of the center of the distal end 102 of the static magnetic field source 101. In such a manner, the device 100 may be shaped as a wand that may be easily maneuvered in the mouth of the examinee. Optionally, the resonator 104 made of dielectric material with high permittivity, such as $TiO_2$ or $SrTiO_3$. The engagement is performed so that the intra-tooth space of the tooth is placed at the probing space in front of the distal end 102. It should be noted that the limited size of the resonator 104 allows easily maneuvering it toward a desired engagement with a certain tooth. Optionally, the micro resonator 104 is sized and shaped so that the probing space overlaps with the enamel portion of the tooth during the engagement. Optionally, the micro resonator 104 is an annular micro resonator 104 mounted so that its central inner space overlaps the central region of the magnetic field where the homogeneity is between 50 ppm and 500 ppm. The device 100 further includes a transmission line 105 that feeds the micro resonator 104 to generate the microwave magnetic field at the probing space.

As described above, the probing space has a limited active volume of less than about 2 $mm^3$ that is optionally designed to be located at the center of the enamel of a typical foretooth. This provides accurate measurement from within the bulk on the tooth from a well defined volume so that the spin concentration may be readily calculated from the spin signal. Optionally, the micro resonator is set to generate a relatively high microwave magnetic field for a given incident microwave power (in the range of between about 2 Gauss per $\sqrt{}$ Watt and about 20 Gauss per $\sqrt{}$ Watt). Optionally, microwave magnetic field of the resonator 104 operates at a frequency in a range of between 2 GHz and 18 GHz.

Optionally, the micro resonator 104 is a dielectric resonator, for example as defined in Aharon Blank et. al., ESR imaging in solid phase down to sub-micron resolution: methodology and applications, Phys. Chem. Chem. Phys., 2009, 11, 6689-6699, which is incorporated herein by reference. Optionally, the resonator is a dielectric ring resonator that has an outer radius, which is about 2.5 times larger than its height. Optionally, the resonator is made of a material having a permittivity of at least 100. Optionally, the resonator is made of rutile single crystal ($TiO_2$). It is excited by a loop at the end of a transmission line, which is optionally a thin semi-rigid coaxial transmission line. For example, the loop has an outer diameter of about 0.4 mm. The loop is optionally placed between the static magnetic field source 101 and the micro resonator 104. Optionally an axis passing via the center of the loop is parallel, and optionally overlaps to an axis passing via the center of the hollow space of the annular micro resonator 104. The resonator 104 is optionally constructed from a flat piece of single crystal in which the C-axis of the crystal is in the plane of the resonator ring, resulting in an average permittivity of about 125. For example, if the resonator operates at a frequency of about 17 GHz and thus its outside diameter is 2.4 mm, its inside diameter is 0.9 mm and its height is 0.5 mm.

The excitation geometry and the calculated fields for such resonator at the resonance frequency are shown in FIG. 4 of Aharon Blank et. al., ESR imaging in solid phase down to sub-micron resolution: methodology and applications, Phys. Chem. Chem. Phys., 2009, 11, 6689-6699, which is incorporated herein by reference.

The device 100 further includes a spectrometer 106 that produces the microwave excitation signal and acquires and analyzes the returned EPR signal from the sample microwave magnetic field. Based on the signal it computes the dose of ionizing radiation absorbed in the tooth accordingly, for example as further described below. The analysis, which is optionally performed by applying an EPR dosimetry analysis, allows measuring minimal radiation doses of less than 1 Gray (Gy), for example about 0.25 Gray (Gy) and up to higher level of radiation doses (1000 Gy) in a probing space in an intra bone volume that is optionally less than 2 $mm^3$.

The probing space defines a sweet spot that is sized and shaped an overlap with the intra bone volume. As described above, the probing space optionally overlaps the enamel of the teeth. As the EPR signal is located principally in the enamel of the teeth, such an embodiment the sensitive volume of the micro resonator 104 increases as the amount of enamel in the probing space is maximized. A collection of paramagnetic centers in the probing space, such as free radicals, is exposed to microwaves.

One method of acquiring the EPR signal is by increasing the static magnetic field in the tooth, the gap between the energy states changes until it matches the energy of the microwaves. At this point the unpaired electrons move between their spin states. This is often referred to as continuous wave EPR, since the microwave is always on. Since there typically are more electrons in the lower state, due to the Boltzmann distribution, there is a net absorption of energy, and it is this absorption which is monitored and converted into a spectrum to compute the dose of ionizing radiation absorbed in the tooth. Another optional method is to use pulsed EPR. In this method microwave pulses are applied at a frequency that closely matches the applied static field. This excites the spins, which in return start to precess and produce an "echo" signal in the resonator, which can be amplified and detected by the spectrometer for further processing.

The combined effect of the relatively high static magnetic field and the high microwave magnetic field which is generated by the micro-resonator 104 leads to a probing space with high spin sensitivity that result in an overall improved signal. It should be noted that the high spin sensitivity is provided even though the volume of measurement is about 2 orders of magnitude smaller than the currently used measurement systems which are based on the analysis the whole volume of one or more full teeth. Optionally, both the magnetic field and the microwave magnetic field are generated outside the body of the device, in front of its distal end. This facilitates the maneuvering of the probing space to overlap with the intra bone volume of a single probed tooth.

Optionally, the device 100 includes a handle 108 that is connected to the proximal end 107 of the static magnetic field source 101 and allows the user to direct the micro resonator 104 to an engagement with one of the teeth. As used herein, an engagement with a tooth means a position in proximity to the tooth, for example few millimeters therefrom or in touch with the tooth.

It should be noted that devices for estimating a dose of ionizing radiation absorbed in teeth, such as molar teeth, generate a large static magnetic field for resolving electron-spin in a volume of more than 2.5 mm$^3$. For generating such a relatively large static magnetic field, the devices use relatively large permanent or electromagnets having a diameter of more than 10 cm, for example 50 cm. respectively, relatively large resonant excitation/detection coils are used. Such devices cannot and are not manually maneuvered in proximity and/or in the mouth of an examinee due to their size and/or weight. Unlike the present device that may be easily and optionally manually maneuvered toward engagement with a foretooth, these devices are based on stationary electro magnets which maneuvered to be placed in proximity to and/or in the mouth of an examinee and therefore their positioning process is complicated. Even a device with a single-sided magnet having a diameter of about 12 cm and for generating a probing space of 5 mm$^3$ is too large and heavy to be manually and easily maneuvered as it requires accurate positioning outside the mouth in order for its homogenous spot to fall exactly inside a desired tooth. Moreover, a device which operates at fields which are relatively low, for example less than 0.2 T, has low accuracy level, inter alia as it works in conjunction with a loop resonator that examined the entire molar tooth and is relatively insensitive and suffers from the drawbacks motioned above of unknown tooth volume and sensitivity to surface defects.

Reference is now also made to FIGS. 6 and 7, which are respectively a schematic illustration of an exemplary device 600 of estimating a dose of ionizing radiation absorbed in a single tooth and a blowup of its distal end, according to some embodiments of the present invention. The static magnetic field source 101 is optionally as depicted in FIG. 3. The device includes a dielectric annular resonator 601 supported by a supporting element 602 sized and shaped to support the mounting of the annular resonator 601 around and/or in front of an incisor of an examinee, optionally few millimeters therefrom. The aforementioned transmission line 105 is placed in a feed 603 that is placed along the longitudinal axis of the static magnetic field source 101. The microwave field is generated by the annular microwaves fed by the transmission line 105 to the resonator 601.

Optionally, the transmission line which is placed in the feed 603 is connected to a spectrometer that is optionally an electron paramagnetic resonance (EPR) spectrometer. Numeral 604 depicts an exemplary connection for allowing the connection to the spectrometer. The transmission line allows the spectrometer 604 receives the EPR single received from the microwave magnetic field and analyzes it to compute a dose of ionizing radiation absorbed in the tooth. The analysis is performed using known dosimetry methods and values, for example as described in David A. Schauer, Electron paramagnetic resonance (EPR) in medical dosimetry, Radiation Measurements 41 (2007) S117-S123, which is incorporated herein by reference.

Optionally, the outputs of the spectrometer, which processed by a computing unit, such as a CPU or a DSP for estimating the radiation effect of the measured dose and/or to determine whether an alarm should be generated. The computing unit is optionally connected to a presentation unit, such as a screen, that allows presenting the dose, the estimated effect, and/or an alarm. The computing unit is optionally a client terminal, such as a personal computer, a Smartphone, a tablet and the like.

Reference is now made to FIG. 8, which is a flowchart of a method of estimating a dose of ionizing radiation absorbed in a portion of a tooth, according to some embodiments of the present invention. Optionally, the method is implemented using the device depicted in FIG. 1. First, as shown at 701, a static magnetic field with homogeneity in a range of between 50 ppm and 500 ppm or static gradient of 0.1-10 T/m (in general—the desired spatial field profile) in a probing space having a volume of less than 2 mm$^3$ inside a single tooth, such as a foretooth is generated. Optionally, the volume is less than 1 mm$^3$, for example a cylindrical volume having a diameter of about 1 mm and a height of about 0.5. Such a volume may be generated when using a device as depicted in FIG. 6. Optionally, the magnate field and/or the homogeneous portion thereof do not exceed the boundaries of the tooth. As the probing space in a foretooth, the device 100 may be easily maneuvered, optionally manually, to engagement therewith. The static magnetic field resolves different electron-spin levels, as described above. The magnetic field is optionally of more than 0.2 T, for example about 0.260 T. The applied magnetic field, which is optionally static, resolves different electron-spin levels.

Now, as shown at 702, a microwave magnetic field is generated at the probing space. The microwave magnetic field and the portion of the magnetic field with the desired spatial field dependence are overlapping, or substantially overlapping. The probing space is optionally generated by a resonator placed in proximity to the single tooth, for example an annular resonator which encircles a portion of the tooth, for example similarly to the described above. The microwave magnetic field microwave magnetic is optionally generated by electromagnetic (EM) energy having a frequency in a range of between 2 GHz and 18 GHz.

Now, as shown at 703, the EPR signal, based on continuous wave (CW) or pulsed excitation/detection schemes, is analyzed to compute a dose of ionizing radiation absorbed in the portion of the tooth. The analysis includes analyzing the EPR signal intercepted, as shown at 704, detecting and/or estimating the absorbed dose of ionizing radiation in the portion of the tooth. The detection and/or estimation may be performed according to known EPR tests, for example as described above. The estimation and/or detection may be displayed to an operator, sent to a remote control unit, and/or activating an alerting module or device.

It is expected that during the life of a patent maturing from this application many relevant methods and devices will be developed and the scope of the term spectrometer, transmission line, and computing is intended to include all such new technologies a priori.

As used herein the term "about" refers to ±10%.

The terms "comprises", "comprising", "includes", "including", "having" and their conjugates mean "including but not limited to". This term encompasses the terms "consisting" of and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and the include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device of estimating a dose of ionizing radiation absorbed in an intra bone volume, comprising:
    a static magnetic field source adapted to generate a substantially static magnetic field in a probing space having a volume of less than 2 cubic millimeter ($mm^3$), said probing space being placed in front of a distal end of static magnetic field source, said static magnetic field source being sized and shaped to maneuver said probing space to overlap with an intra bone volume of said bone;
    a micro resonator mounted in adjacent to said distal end; and
    at least one transmission line which feeds said resonator so as to generate a microwave magnetic field at said probing space,
    wherein said micro resonator acquires, from said probing space, a signal returned from to said generated microwave magnetic field and indicative of radiation induced paramagnetic defects in said probing space so as to allow a spectrometer to compute a dose of ionizing radiation absorbed in a portion of a bone placed in said probing space according to an analysis of said signal.

2. The device of claim 1, wherein said signal is an electron spin resonance (ESR) signal.

3. The device of claim 1, wherein said static magnetic field source is adapted to form said static magnetic field at a distance of at least 3 mm in front of said distal end.

4. The device of claim 1, wherein said static magnetic field source having a diameter of less than 5 centimeter (cm).

5. The device of claim 1, wherein said static magnetic field source having a longitudinal dimension of less than 15 centimeter (cm).

6. The device of claim 1, further comprising a handle for allowing a user to manually locate said distal end in proximity to said bone.

7. The device of claim 1, wherein said static magnetic field having at least 0.2 Tesla (T) in a homogeneity level between 50 and 500 parts per million (ppm) in a region of less than 1 $mm^3$.

8. The device of claim 1, wherein said static magnetic field having a gradient in a range between about 0.1 T/m and about 10 T/m along a main axis of said probing space.

9. The device of claim 1, wherein said probing space having a diameter of less than about 1 mm and a height of less than about 0.5.

10. The device of claim 1, wherein said resonator is annular.

11. The device of claim 10, wherein said static magnetic field is substantially maximal at a point just above the center of said resonator.

12. The device of claim 1, wherein said resonator is a dielectric resonator.

13. The device of claim 1, wherein said spectrometer comprises an electron paramagnetic resonance (EPR) spectrometer.

14. The device of claim 1, wherein said static magnetic field source comprises at least one elongated magnetic element in a tubular formation having a central longitudinal axis, said resonator being mounted on said longitudinal axis.

15. The device of claim 1, wherein said resonator operates at a frequency between 2 GHz and 18 GHz.

16. A method of estimating a dose of ionizing radiation absorbed in an intra bone volume, said method comprising:
generating a magnetic field of having at least one of a gradient in a range between about 0.1 Tesla (T)/meter (m) and about 10 T/m along a main axis of a probing space and at least 0.2 T with homogeneity in a range of between 50 and 500 parts per million (ppm), said magnetic field being in a region of less than 2 cubic millimeter ($mm^3$) in intra bone volume of a bone;
generating a microwave magnetic field at said region;
acquiring a signal indicative of radiation induced paramagnetic defects in said probing space from said region; and
analyzing said signal, to compute a dose of ionizing radiation absorbed in an intra bone volume of said bone.

17. The method of claim 16, wherein said bone is a single tooth.

18. The method of claim 17, wherein said single tooth is a foretooth.

19. The method of claim 16, wherein said generating comprises resonating an electromagnetic (EM) energy at a frequency between 2 GHz and 18 GHz.

20. The method of claim 16, further comprising displaying said radiation dose.

21. The method of claim 16, wherein said analyzing comprises analyzing an electron paramagnetic resonance (EPR) signal from said region.

22. The method of claim 16, wherein said dose is a minimal measurable radiation dose of less than 0.25 Gray (Gy) in said region.

23. A handheld probe of estimating a dose of ionizing radiation absorbed in an intra bone volume, comprising:
a static magnetic field source having at least one elongated magnetic element in a tubular formation having a first diameter of less than 5 centimeters, said static magnetic field source being adapted to generate a substantially static magnetic field in a probing space in front of a distal end of said at least one elongated magnetic element;
a micro resonator mounted in adjacent to said distal end and having a second diameter smaller than said first diameter; and
at least one transmission line which feed said resonator so as to generate an microwave magnetic field at said probing space;
wherein said micro resonator acquires a signal returned from said microwave magnetic field at said probing space and indicative of radiation induced paramagnetic defects in said probing space to allow a spectrometer to compute a dose of ionizing radiation absorbed in a tooth placed in said probing space according to an analysis of said signal.

24. The handheld probe of claim 23, wherein said at least one elongated magnetic element is less than 15 centimeters (cm) long.

* * * * *